United States Patent
Fleckenstein et al.

(10) Patent No.: US 6,177,080 B1
(45) Date of Patent: Jan. 23, 2001

(54) POLYPEPTIDES ENCODED BY KAPOSI SARCOMA-ASSOCIATED HERPES VIRUS THE USE THEREOF IN DIAGNOSIS AND THERAPY

(75) Inventors: Bernhard Fleckenstein, Wiesenthau; Jens-Christian Albrecht, Fürth; Frank Neipel, Uttenreuth; Dieter Lang, Dietzenbach, all of (DE)

(73) Assignee: Biotest AG (DE)

(*) Notice: Under 35 U.S.C. 154(b), the term of this patent shall be extended for 0 days.

(21) Appl. No.: 09/112,248

(22) Filed: Jul. 8, 1998

(30) Foreign Application Priority Data

Jul. 11, 1997 (EP) .................................................. 97111879

(51) Int. Cl.$^7$ ......................... A61K 39/12; A61K 39/245

(52) U.S. Cl. ..................................... 424/186.1; 424/204.1; 424/229.1; 424/230.1; 435/5; 435/7.1; 435/7.92; 435/7.94; 435/235.1; 530/350; 530/300; 536/23.72

(58) Field of Search .............................. 424/186.1, 229.1, 424/204.1, 230.1; 435/5, 7.1, 7.92, 7.94, 235.1; 530/350, 300; 536/23.72

(56) References Cited

U.S. PATENT DOCUMENTS

| | | | |
|---|---|---|---|
| 5,656,475 | 8/1997 | Nick et al. | 435/235.1 |
| 5,670,352 | 9/1997 | Biesinger-Zwosta et al. | 435/172.3 |
| 5,814,475 | 9/1998 | Neipel et al. | 435/69.1 |

FOREIGN PATENT DOCUMENTS

| | | |
|---|---|---|
| 9416062 | 7/1994 | (WO). |
| 9606159 | 8/1995 | (WO). |
| 9804284 | 7/1997 | (WO). |
| 9803657 | 1/1998 | (WO). |

OTHER PUBLICATIONS

EMBL Databank Entry KSU75698; Access No. U75698 (Version 2), Feb. 17, 1997, see Nucleotide 75915 to 76508.

Andre et al., "Detection of antibodies against viral capsid proteins of human herpesvirus 8 in AIDS–associated Kaposi's sarcoma" *J. Mol. Med.* 75:145–152 (1997).

Archibald et al., "Evidence for a Sexually Transmitted Cofactor for AIDS–Related Kaposi's Sarcoma in a Cohort of Homoesexual Men" *Epidemiology* 3(3):203–209 (1992).

Arvanitakis et al., "Human herpesvirus KSHV encodes a constitutively active G–protein–coupled receptor linked to cell proliferation" *Nature* 385:347–350 (1997).

Beral et al., "Risk of Kaposi's sarcoma and sexual practices associated with faecal contact in homosexual or bisexual men with AIDS" *The Lancet* 339:632–635 (1992).

Blasig et al., "Monocytes in Kaposi's Sarcoma Lesions Are productive Infected by Human Herpesvirus 8" *J. Virol.* 71(10):7963–7968 (1997).

Boshoff et al., "Establishing a KSHV+ Cell Line (BCP–1) From Peripheral Blood and Characterizing Its Growth in Nod/SCID Mice" *Blood* 91(5):1671–1679 (1998).

Boshoff et al., "Kaposi's Sarcoma–Associated Herpesvirus" *Advances in Cancer Research* 57–86 (1998).

Burger et al., "Human Herpesvirus Type 8 Interleukin–6 Homologue Is Functionally Active on Human Myeloma Cells" *Blood* 91(6):1858–1863 (1998).

Cesarman et al., "Kaposi's sarcoma–associated herpes virus contains G protien–coupled receptor and cyclin D homologs which are expressed in Kaposi's sarcoma and malignant lymphoma" *J. Virol.* 70:8218–8223 (1996).

Chan et al., "Identification and Characterization of Human Herpesvirus–8 Lytic Cycle–Associated ORF 59 Protein and the Encoding cDNA by Monoclonal Antibody" *Virology* 240:118–126 (1998).

Chang et al., "Identification of herpes–like DNA sequences in AIDS–associated Kaposi's Sarcoma" *Science* 266:1865–1869 (1994).

Cheng et al., "A Bcl–2 homolog encoded by Kaposi sarcoma–associated virus, human herpesvirus 8, inhibits apoptosis but does not heterodimerize with Bax or Bak" *Proc. Natl. Acad. Sci.* 94:690–694 (1997).

(List continued on next page.)

*Primary Examiner*—Ali Salimi
(74) *Attorney, Agent, or Firm*—Stephanie Seidman; Heller Ehrman White & McAuliffe LLP

(57) ABSTRACT

The invention relates to polypeptides of the Kaposi sarcoma-associated herpes virus which have a part-sequence of at least 10 consecutive amino acids from the sequence

```
Met Ser Ser Thr Gln Ile Arg
Thr Glu Ile Pro Val Ala Leu
Leu Ile Leu Cys Leu Cys Leu
Val Ala Cys His Ala Asn Cys
Pro Thr Tyr Arg Ser His Leu
Gly Phe Trp Gln Glu Gly Trp
Ser Gly Gln Val Tyr Gln Asp
Trp Leu Gly Arg Met Asn Cys
Ser Tyr Glu Asn Met Thr Ala
Leu Glu Ala Val Ser Leu Asn
Gly Thr Arg Leu Ala Ala Gly
Ser Pro Ser Ser Glu Tyr Pro
Asn Val Ser Val Ser Val Glu
Asp Thr Ser Ala Ser Gly Ser
Gly Glu Asp Ala Ile Asp Glu
Ser Gly Ser Gly Glu Glu Glu
Arg Pro Val Thr Ser His Val
Thr Phe Met Thr Gln Ser Val
Gln Ala Thr Thr Glu Leu Thr
Asp Ala Leu Ile Ser Ala Phe
Ser Gly Val Leu His Val Ser
Thr Val Ile Pro Arg Asn Trp
Val Asn Arg Arg Cys Val Gly
Ile Lys Arg Asn Leu Thr Phe
Cys Leu Ile Tyr Arg Ile Ile
Phe Ile Trp Gly Thr Ile Gln
Asp His Ala Asn Ser Arg Ile
Thr Gly Arg Arg Lys Arg Gln
Lys
``` and to the use thereof in therapy and diagnosis.

34 Claims, 6 Drawing Sheets

OTHER PUBLICATIONS

Dictor "Human Herpesvirus 8 and Kaposi's Sarcoma" *Seminars in Cutaneous Medicine and Surgery* 16(3):181–187 (1997).

Gao et al., "KSHV antibodies among Americans, Italians and Ugandans with and without Kaposi's sarcoma" *Nature Med* 2(8):925–928 (1996).

Kedes et al., "Identification of the Gene encoding the Major Latency–associated Nuclear Antigen of the Kaposi's Sarcoma–associated Herpesvirus" *J.Clin.Invest.* 100(10):2606–2610 (1997).

Kedes et al., "The seroepidemiology of human herpesvirus 8 (Kaposi's sarcoma–associated herpesvirus): Distribution of infection in KS risk groups and evidence for sexual transmission" *Nature Med* 2(8):918–924 (1996).

Kemeny et al., "Kaposi's sarcoma–associated herpesvirus/human herpesvirus–8: A new virus in human pathology" *J Am Acad Dermatol* 37:107–113 (1997).

Lee et al., "Deregulation of cell growth by the K1 gene of Kaposi's sarcoma–associated herpes–virus" Nat. med. 4:435–440 (1998).

Levy "Three new human herpesviruses (HHV6, 7, and 8)" *Lancet* 349:558–563 (1997).

Li et al., "Kaposi's Sarcoma–Associated Herpesvirus Encodes a Functional Cyclin" *J. Virol.* 71(3):1984–1991 (1997).

Li et al., "Kaposi's sarcoma–associated herpesvirus viral interferon regulatory factor" *J. Virol.* 72:5433–5440.

Lifson et al., "Kaposi's Sarcoma in a Cohort of Homosexual and Bisexual Men" *Amer J of Epidem* 131(2):221–231 (1990).

Lin et al., "Identification, Expression, and Immunogenicity of Kaposi's Sarcoma–Associated Herpesvirus–Encoded Small Viral Capsid Antigen" *J of Virol* 71(4):3069–3076 (1997).

Lock et al., "Development of a quantitative competitive polymerase chain reaction for human herpesvirus 8" *J. Virol. Meth.* 64:19–26 (1997).

Moore et al., "Primary characterization of of a herpesvirus agent associated with Kaposi's sarcoma" *J. Virol.* 70:549–558 (1996).

Moore et al., "Molecular mimicry of human cytokine and cytokine response pathway genes by KSHV" *Science* 274:1739–1744 (1996).

Moore et al., "Detection of Herpesvirus–like DNA Sequences in Kaposi's Sarcoma in Patients With and Those Without HIV Infection" *New England J of Medicine* 332(18):1181–1185 (1995).

Muralidhar et al., "Identification of Kaposin (open reading frame K12) as a human herpesvirus 8 (Kaposi's sarcoma–associated herpesvirus) transforming gene" *J. Virol.* 72:4980–8 (1998).

Neipel et al., "Cell–Homologous Genes in the Kaposi's Sarcoma–Associated Rhadinovirus Human Herpesvirus 8: Determinants of Its Pathogenicity?" *J. Virol* 71(6):4187–4192 (1997).

Neipel et al., "Human Herpesvirus 8—the First Human Rhadinovirus" *J of the Nat Canc Inst Monographs* No. 23 (1998).

Neipel et al., "Human Herpesvirus 8 Encloses a Homolog of Interleukin–6" *J. of Virol* 71(1):839–842 (1997).

Nicholas et al., "A Single 13–Kilobase Divergent Locus in the Kaposi Sarcoma Associated Herpesvirus (Human Herpesvirus 8) Genome Contains Nine Open Reading Frames That Are Homologous to or Related to Cellular Proteins" *J. Virol* 71(3):1963–1974 (1997).

O'Neill et al., "Open Reading Fram 26 of Human Herpesvirus 8 Encodes a Tetradecanoyl Phorbol Acetate– and Butyrate–Inducible 32–Kilodalton Protein Expressed in a Body Cavity–Based Lymphoma Cell Line" *J of Virolog* 71(6):4791–4797 (1997).

Raab et al., "The immunigenic glycoprotein gp35-37 of human herpesvirus 8 is encoded by open reading frame K8.1" J. Virol. 72:6725–31 (1998).

Ruger, "Search for DNA Sequences of Human Cytomegalovirus in Kaposi's Sarcoma Tissues with Cloned Probes" *Antibiot. Chemother.* 32:43–47 (1984).

Russo et al., "Nucleotide sequence of the Kaposi's sarcoma–associated herpesvirus (HHV8)" Proc. Natl. Acad. Sci. U.S.A. 93:14862–14867 (1996).

Sarid et al., "Transcription mapping of the Kaposi's sarcoma–associated herpesvirus (human herpesvirus 8) genome in a body cavity–based lymphoma cell line (BC–1)" *J. Virol.* 72:1005–12 (1998).

Schechter et al., "Geographic and Birth Cohort Associations of Kaposi's Sarcoma among Homosexual Men in Canada" *Amer J of Epidem* 134(5):485–488 (1991).

Simpson et al., "Prevalence of Kaposi's sarcoma associated herpesvirus infection measured by antibodies to recombinant capsid protein and latent immunofluorescence antigen" *The Lancet* 348:1133–1138 (1996).

Sturzl, "Expression of HHV–8 latency–associated T0.7 RNA in spindle cells and endothelial cells of AIDS–associated, classical and African Kaposi's Sarcoma" *Int. J. Cancer* 72:68–71 (1997).

Ünal et al., "The Protease and the Assembly Protein of Kaposi's Sarcoma–Associated Herpesvirus (Human Herpesvirus 8)" *J of Virolog* 71(9):7030–7038 (1997).

Zhong et al., "Restricted expression of Kaposi's sarcoma–associated herpesvirus (human herpesvirus 8) genes in Kaposi's sarcoma" *Proc. Natl. Acad. Sci. U.S.A.* 93:6641–6646 (1996).

```
Met Ser Ser Thr Gln Ile Arg Thr Glu Ile Pro Val Ala Leu Leu Ile
Leu Cys Leu Cys Leu Val Ala Cys His Ala Asn Cys Pro Thr Tyr Arg
Ser His Leu Gly Phe Trp Gln Glu Gly Trp Ser Gly Gln Val Tyr Gln
Asp Trp Leu Gly Arg Met Asn Cys Ser Tyr Glu Asn Met Thr Ala Leu
Glu Ala Val Ser Leu Asn Gly Thr Arg Leu Ala Ala Gly Ser Pro Ser
Ser Glu Tyr Pro Asn Val Ser Val Ser Val Glu Asp Thr Ser Ala Ser
Gly Ser Gly Glu Asp Ala Ile Asp Glu Ser Gly Ser Gly Glu Glu Glu
Arg Pro Val Thr Ser His Val Thr Phe Met Thr Gln Ser Val Gln Ala
Thr Thr Glu Leu Thr Asp Ala Leu Ile Ser Ala Phe Ser Gly Val Leu
His Val Ser Thr Val Ile Pro Arg Asn Trp Val Asn Arg Arg Cys Val
Gly Ile Lys Arg Asn Leu Thr Phe Cys Leu Ile Tyr Arg Ile Ile Phe
Ile Trp Gly Thr Ile Gln Asp His Ala Asn Ser Arg Ile Thr Gly Arg
Arg Lys Arg Gln Lys
```

Fig. 1

```
ATG AGT TCC ACA CAG ATT CGC ACA GAA ATC CCT GTG GCG CTC CTA ATC
CTA TGC CTT TGT CTG GTG GCG TGC CAT GCC AAT TGT CCC ACG TAT CGT
TCG CAT TTG GGA TTC TGG CAA GAG GGT TGG AGT GGA CAG GTT TAT CAG
GAC TGG CTA GGC AGG ATG AAC TGT TCC TAC GAG AAT ATG ACG GCC CTA
GAG GCC GTC TCC CTA AAC GGG ACC AGA CTA GCA GCT GGA TCT CCG TCG
AGT GAG TAT CCA AAT GTC TCC GTA TCT GTT GAA GAT ACG TCT GCC TCT
GGG TCT GGA GAA GAT GCA ATA GAT GAA TCG GGG TCG GGG GAG GAA GAG
CGT CCC GTG ACC TCC CAC GTG ACT TTT ATG ACA CAA AGC GTC CAG GCC
ACC ACA GAA CTG ACC GAT GCC TTA ATA TCA GCC TTT TCA GGT GTA TTA
CAC GTT TCA ACT GTA ATC CCT CGC AAT TGG GTA AAC CGT CGG TGT GTA
GGG ATA AAG CGT AAC CTT ACG TTC TGT CTC ATC TAC AGG ATC ATA TTC
ATC TGG GGA ACC ATC CAG GAC CAC GCG AAT TCG CGT ATC ACC GGT CGC
AGA AAA CGG CAG AAA TAG
```

Fig. 2

Nucleotide position of ORF K8.1 in the HHV8 genome

POLYPEPTIDES ENCODED BY KAPOSI SARCOMA-ASSOCIATED HERPES VIRUS THE USE THEREOF IN DIAGNOSIS AND THERAPY

Kaposi sarcoma is a vascular tumor of the skin which is now of great clinical and epidemiological importance. Originally, Kaposi sarcoma occurred rarely and predominantly in the older male population of south and south east Europe (especially Italy and Greece).

With the spread of human immunodeficiency virus (HIV), Kaposi sarcoma has achieved considerable importance and now represents one of the commonest manifestations in AIDS patients.

In recent years, a herpes virus has been discovered to occur in Kaposi sarcoma tissue from AIDS patients in a very high percentage. This virus has been referred to as Kaposi sarcoma-associated herpes virus (KSHV) or HHV-8. Russo et al. have recently published the nucleotide sequence of Kaposi sarcoma-associated herpes virus [*Proc.Natl.Acad.Sci., USA*, Vol. 93 (December 1996), pages 14862–14867].

The nucleotide sequence of KSHV shows noticeable sequence homologies with known gamma-herpesviruses such as, for example, the herpesvirus Saimiri (HVS), which occurs in monkeys, and the Epstein-Barr virus (EBV). Taxonomically, the virus is included in the Rhadinoviridae group.

The genome of the virus comprises about 165 kilobases, and Russo has identified 81 open reading frames within this sequence, of which 66 are homologous with open reading frames of the herpes virus Saimiri.

It has emerged that the genome of KSHV can also be detected in AIDS-independent classical and endemic forms of Kaposi sarcoma, as well as in other rare tumors such as body cavity based lymphoma (BCBL) and Castleman's disease (CD).

The mechanism of transmission of KSHV has not yet been completely elucidated. Since the virus can be detected in sperm, there is unlikely to be any doubt about sexual transmission in homosexual men. However, there must also be another transmission route in endemic areas.

It has not yet been possible to infect cells with KSHV in vitro reliably and with adequate efficiency. There are B-cell culture systems, for example BC-1 and BCBL-1, in which the virus shows latent persistence, and the lytic replication cycle can be stimulated with a phorbol ester, namely tetradecanoylphorbol acetate (TPA).

For constructing the gene bank, Russo et al. used the BC-1 cell line which is coinfected both with KSHV and with Epstein-Barr virus.

By contrast, according to the invention, the BCBL-1 cell line which is infected only with KSHV has been used. When this cell line is induced with TPA, KSHV-specific antigen expression takes place in the cell culture, and the antigens expressed in this way have been employed to provide the polypeptides according to the invention. The lysates of induced BCBL-1 cells were initially investigated.

The cell culture-dependent Western blot and immunofluorescence analyses establish 95% sensitivity with the sera from AIDS patients with Kaposi sarcoma. It was possible to show by these analyses that the seroprevalence of KSHV in homosexual, HIV-positive men is significantly greater than in HIV-positive hemophilia patients, so that it can be assumed that the virus is transmitted by a sexual route. The seroprevalence in the normal population is subject to wide regional variations. The seroprevalence in the USA and northern Europe is below 0.5%, whereas in Italy 5% and in Uganda 50% of the blood samples from healthy blood donors show antibodies against KSHV. It was also possible to show that about 6 to 75 months before the appearance of a Kaposi sarcoma it was possible to detect seroconversion of KSHV antibodies, and a prospective statement about the clinical manifestation of Kaposi sarcoma was possible. Thus detection of KSHV-specific antibodies represents a suitable diagnostic marker for most experts. Because of the considerable technical complexity and the lack of standardization, the existing serological test methods are suitable only for special diagnostic laboratories.

The provision of a recombinant capsid protein encoded by open reading frame 65 (ORF65) has been described. It was possible to show that the C-terminal part of the protein (AA 86-170) has the same serological reactivity as the full-length protein [Simpson et al., *Lancet*, Vol. 348 (October 1996), pages 11033–11038]. Lin et al. also used recombinant OR65 antigen in serological tests for detecting antibodies against Kaposi sarcoma-associated herpes virus. In this case, this is the small viral capsid antigen (sVCA) [*Journal of Virology* (April 1997), pages 3069–3076] which represents the homologous protein to BFRF3 of EBV.

It is therefore one object of the present invention to provide further polypeptides which are suitable for detecting KSHV in standardized and automated methods. Characterization and identification of suitable immunologically reactive antigens is necessary for immunoblots or enzyme-linked immunosorbent assays (ELISA).

The polypeptides according to the invention are encoded by a reading frame which has not previously been identified and is referred to according to the invention as ORF K8.1. This reading frame was identified in the following way:

It was possible to detect in Western blot analyses, with BCBL-1 cells stimulated to lytic KSHV replication with TPA, using sera from particular patients (HIV-positive with Kaposi sarcoma) a protein double band with a molecular weight of about 35–37 kilodaltons. Deglycosilation experiments were carried out to characterize the protein (gp35/37). It emerged from these that the proteins with a migration behavior of 35 and 37 kDa in SDS-polyacrylamide gel electrophoresis (SDS-PAGE) can be converted by deglycosylating enzymes into one protein band with 30 kDa. It was concluded from this that the protein must be a viral glycoprotein which is present in two glycosilated forms in the KSHV-infected cell.

Since the sequence of the KSHV from the BC-1 cell has now been determined, this sequence was screened using various screening criteria to identify a suitable open reading frame. The specific criteria used for this do not comply with the usual rules. Initial screening was only for open reading frames having a start codon (ATG). It was not a requirement that a TATA box precede the start of transcription. It was possible in this way to find open reading frames with start codons which did not comply with the usual Kozack rules. Among the reading frames found in this way, only those reading frames coding for a protein with a molecular weight between 15 and 45 kDa were taken into account. In addition, the sequences selected from the reading frames found in this way were those having an N-glycosilation site. The potential open reading frames found in this way were also limited by the requirement for the presence of a signal peptide. Five of the initially found 41 reading frames met the abovementioned conditions, namely the open reading frames ORF47 (glycoprotein L); K2 (IL6-homologous); ORF70 (thymidylate synthase); K1 and K8.1. ORF70 was not taken into further account subsequently. The coding sequence of ORF47, K2, K1 and K8.1 was in each case cloned into the expression vector pQE9 (from Qiagen), and the proteins were expressed as histidine fusion proteins in *E.coli*. It was possible due to the histidine fusion protein content to purify the proteins using nickel chelate agarose and employ them in Western blot tests. The sera used for this were those which also reacted with the protein gp35/37 in the natural Western blot. Whereas the proteins of reading frames ORF47, K2, K1 showed no reactivity whatsoever, all the sera reacted with the recombinant K8.1 protein. Subsequent reexamination of the publication by Russo et al. revealed that the reading frame ORF K8.1 used according to the invention is not mentioned.

In order to demonstrate that the protein gp35/37 in the natural Western blot with BCBL-1-induced cells is identical to the recombinant protein prepared with the aid of the reading frame ORF K8.1 according to the invention, antibodies from sera from KS-positive patients were bound by means of preparative Western blot analysis to recombinant gp35/37. Antibodies recovered by subsequent elution were then employed in a second Western blot with TPA-induced cells. In this case, only gp35/37 reacted with the antibodies preselected by recombinant polypeptide K8.1. It was thus possible to show the correspondence of gp35/37 in the natural immunoblot with recombinant K8.1. The immunogenic and KSHV-specific properties of gp35/37 are shown by using the recombinant antigen according to the invention in immunoblot and ELISA experiments.

The present invention therefore relates to polypeptides which are characterized in that they have a part-sequence of at least 10 consecutive amino acids from the sequence number of amino acids, namely less than 10 amino acids, are not comprised by the term.

It is also preferred according to the invention to employ part-sequences of the polypeptide K8.1, in particular those constituent regions of the polypeptide which comprise antigenic determinants. The polypeptide K8.1 according to the invention consists of a signal peptide which comprises the first 26 amino acids (Met . . . Ala), and of the recombinant polypeptide, that is to say polypeptide without signal peptide. The latter has 170 amino acids, the sequence starting with Asn and ending with Lys.

Particularly preferred antigenic constituent regions are the polypeptides having the following coordinates:
a) Amino acid 29–59. The polypeptide with 31 amino acids starts with Pro and ends with Glu.
b) Polypeptide between amino acids 73 and 113. The polypeptide with 41 amino acids starts with the amino acid Arg and ends with the amino acid Arg.
c) The polypeptide starts with amino acid 152 and ends with amino acid 196. This polypeptide with 45 amino acids starts with the amino acid Arg and ends with the amino acid Lys.
d) Amino acid 183–196. The polypeptide with 14 amino acids starts with Asp and ends with Lys.

Polypeptides b) and d) are particularly preferred, the latter comprising the 14 C-terminal amino acids which represent a strongly basic region. Combinations of polypeptides a) and b) or b) and d), and of a) and c) are also preferred according to the invention.

The present invention also relates to variants of the polypeptides according to the invention. The skilled worker is aware that the polypeptides may be modified slightly at

```
Met Ser Ser Thr Cln Ile Arg Thr Glu Ile Pro Val Ala Leu
Leu Ile Leu Cys Leu Cys Leu Val Ala Cys His Ala Asn Cys
Pro Thr Tyr Arg Ser His Leu Gly Phe Trp Gln Glu Gly Trp
Ser Gly Gln Val Tyr Gln Asp Trp Leu Gly Arg Met Asn Cys
Ser Tyr Glu Asn Met Thr Ala Leu Glu Ala Val Ser Leu Asn
Gly Thr Arg Leu Ala Ala Gly Ser Pro Ser Ser Glu Tyr Pro
Asn Val Ser Val Ser Val Glu Asp Thr Ser Ala Ser Gly Ser
Gly Glu Asp Ala Ile Asp Glu Ser Gly Ser Gly Glu Glu
Arg Pro Val Thr Ser His Val Thr Phe Met Thr Gln Ser Val
Gln Ala Thr Thr Glu Leu Thr Asp Ala Leu Ile Ser Ala Phe
Ser Gly Val Leu His Val Ser Thr Val Ile Pro Arg Asn Trp
Val Asn Arg Arg Cys Val Gly Ile Lys Arg Asn Leu Thr Phe
Cys Leu Ile Tyr Arg Ile Ile Phe Ile Trp Gly Thr Ile Gln
Asp His Ala Asn Ser Arg Ile Thr Gly Arg Arg Lys Arg Gln
Lys.
```

The term "polypeptide" for the purpose of the present application means compounds which comprise at least 10 amino acids and for which the upper limit of amino acids is about 250 to 300 amino acids. The term thus also comprises compounds which can also be referred to as proteins. oligopeptides, that is to say compounds with a very small certain positions, for example by deletions or replacements of amino acids, with, as a rule, no change in the immunological activity of the polypeptide resulting from, in particular, replacement of one amino acid by an amino acid having the same immunological effect.

The polypeptide according to the invention without the signal peptide has the following sequence:

```
Asn Cys Pro Thr Tyr Arg Ser His Leu Gly Phe Trp Gln Glu
Gly Trp Ser Gly Glri Val Tyr Gln Asp Trp Leu Gly Arg Met
Asn Cys Ser Tyr Glu Asn Met Thr Ala Leu Glu Ala Val Ser
Leu Asn Gly Thr Arg Leu Ala Ala Gly Ser Pro Ser Ser Glu
Tyr Pro Asn Val Ser Val Ser Val Glu Asp Thr Ser Ala Ser
Gly Ser Gly Glu Asp Ala Ile Asp Glu Ser Gly Ser Gly Glu
Glu Glu Arg Pro Val Thr Ser His Val Thr Phe Met Thr Gln
Ser Val Gln Ala Thr Thr Glu Leu Thr Asp Ala Leu Ile Ser
```

-continued
```
Ala Phe Ser Gly Val Leu His Val Ser Thr Val Ile Pro Arg
Asn Trp Val Asn Arg Arg Cys Val Gly Ile Lys Arg Asn Leu
Thr Phe Cys Leu Ile Tyr Arg Ile Ile Phe Ile Trp Gly Thr
Ile Gln Asp His Ala Asn Ser Arg Ile Thr Gly Arg Arg Lys
Arg Gln Lys.
```

Preferred part-sequences of the polypeptide according to the invention have at least 14, 25, 30 or, particularly preferably, 40 amino acids which represent fragments of the stated sequences.

The polypeptides according to the invention correspond in respect of the sequence to a protein encoded by a Kaposi sarcoma-associated herpes virus. Antibodies from a patient infected with this virus therefore react specifically with the polypeptides according to the invention. Specifically means that an antigen-antibody reaction indicates that an infection with KSHV is present. It is necessary for this purpose that there is no cross-reactivity with another virus or with other antigens. A nonspecific reaction of this type would lead to false-positive results.

The polypeptides according to the invention can be prepared in various ways. Chemical synthesis can be chosen for shorter polypeptides. The chemical synthesis of polypeptides is well known per se and normally takes place on a solid phase. However, the disadvantages of the chemical synthesis are that, in the case of longer polypeptides, products which are incorrect in the sequence because wrong amino acids have been incorporated are produced, and that products of this type can be removed only poorly from the required polypeptides. In addition, chemically synthesized polypeptides are often incorrectly folded.

Longer polypeptides in particular are therefore prepared by genetic manipulation methods known per se in host cells.

For this purpose, the coding nucleic acid is incorporated into a suitable vector, for example into an expression plasmid. Expression of the polypeptides according to the invention can then take place either in prokaryotic host cells, for example E.coli. However, these products have no glycosilation because bacteria have no glycosilation mechanisms.

As an alternative to this, expression can take place in eukaryotic host cells. Suitable examples thereof would be yeast cells, insect cells or else mammalian cells grown in cell cultures.

The present invention also relates to test kits for detecting an infection with a Kaposi sarcoma-associated herpes virus in a mammal, which comprise at least one polypeptide according to the invention.

The term "test kit" means a suitable arrangement for detecting antibodies. This may comprise prepared kits which can be employed in diagnostic laboratories for detecting the antibodies. Possible examples of test kits of this type comprise Western blot strips or ELISA plates already coated with the polypeptides according to the invention. In addition, a test kit may also comprise other components required for carrying out the test, such as, for example, the detection components used to detect the polypeptide-specific antibody complex.

Such another component for detecting the complex comprising a polypeptide according to the invention and at least one antibody specifically bound thereto can be an anti-antibody or another antibody which is directed against a polypeptide according to the invention.

This component for detecting the complex may be labeled, for example, with an enzyme which catalyzes a color reaction (for example peroxydase). However, it is also possible for the polypeptide to be labeled. It is possible in the preparation by genetic manipulation for the polypeptide to be expressed as fusion protein, the fusion portion making labeling or removal easily possible.

The polypeptides according to the invention are thus preferably used for detecting an infection with a Kaposi sarcoma-associated herpes virus.

The invention also relates to nucleic acid constructs for the preparation by genetic manipulation of a polypeptide, which comprise the nucleic acid sequence

```
ATG AGT TCC ACA CAG ATT CGC ACA GAA ATC CCT GTG GCG CTC
CTA ATC CTA TGC CTT TGT CTG GTG GCG TGC CAT GCC AAT TGT
CCC ACG TAT CGT TCG CAT TTG GGA TTC TGG CAA GAG GGT TGG
AGT GGA CAG GTT TAT CAG GAC TGG CTA GGC AGG ATG AAC TGT
TCC TAC GAG AAT ATG ACG GCC CTA GAG GCC GTC TCC CTA AAC
GGG ACC AGA CTA GCA GCT GGA TCT CCG TCG AGT GAG TATCCA
AAT GTC TCC GTA TCT GTT GAA GAT ACG TCT GCC TCT GGG TCT
GGA GAA GAT GCA ATA GAT GAA TCG GGG TCG GGG GAG GAA GAG
CGT CCC GTG ACC TCC CAC GTG ACT TTT ATG ACA CAA AGC GTC
CAG GCC ACC ACA GAA CTG ACC GAT GCC TTA ATA TCA GCC TTT
TCA GGT GTA TTA CAC GTT TCA ACT GTA ATC CCT CGC AAT TGG
GTA AAC CGT CGG TGT GTA GGG ATA AAG CGT AAC CTT ACG TTC
TGT CTC ATC TAC AGG ATC ATA TTC ATC TGG GGA ACC ATC CAG
GAC CAC GCG AAT TCG CGT ATC ACC GGT CGC AGA AAA CGG CAG
AAA TAG
``` or a part-sequence thereof with at least 30 nucleotides.

The term "nucleic acid construct" means according to the invention a nucleic acid structure which comprises a suitable nucleic acid sequence coding for a polypeptide according to the invention and which makes it possible for this construct to be replicated in the host cell and for the required polypeptide to be expressed in the host cell. The nucleic acids employed according to the invention comprise DNA in a preferred embodiment.

In a preferred embodiment, a nucleic acid construct of this type is an expression vector, that is to say a nucleic acid structure which is itself able to replicate in the introduced host cell and causes the host cell to express the polypeptide according to the invention.

In another embodiment of the invention, a partial sequence with 15 to 35 nucleotides from the nucleic acid sequence

```
ATG AGT TCC ACA CAG ATT CGC ACA GAA ATC CCT GTG GCG CTC
CTA ATC CTA TGC CTT TGT CTG GTG GCG TGC CAT GCC AAT TGT
CCC ACG TAT CGT TCG CAT TTG GGA TTC TGG CAA GAG GGT TGG
AGT GGA CAG GTT TAT CAG GAC TGG CTA GGC AGG ATG AAC TGT
TCC TAC GAG AAT ATG ACG GCC CTA GAG GCC GTC TCC CTA AAC
GGG ACC AGA CTA GCA GCT GGA TCT CCG TCG AGT GAG TAT CCA
AAT GTC TCC GTA TCT GTT GAA GAT ACG TCT GCC TCT GGG TCT
GGA GAA GAT GCA ATA GAT GAA TCG GGG TCG GGG GAA GAG
CGT CCC GTG ACC TCC CAC GTG ACT TTT ATG ACA CAA AGC GTC
CAG GCC ACC ACA GAA CTG ACC GAT GCC TTA ATA TCA GCC TTT
TCA GGT GTA TTA CAC GTT TCA ACT GTA ATC CCT CGC AAT TGG
GTA AAC CGT CGG TGT GTA GGG ATA AAG CGT AAC CTT ACG TTC
TGT CTC ATC TAC AGG ATC ATA TTC ATC TGG GGA ACC ATC CAG
GAC CAC GCG AAT TCG CGT ATC ACC GGT CGC AGA AAA CGG CAG
AAA TAG
``` or a nucleic acid sequence complementary thereto can be used for detecting an infection with a Kaposi sarcoma-associated herpes virus by means of the polymerase chain reaction.

In the detection method using the polymerase chain reaction, so-called primers, that is to say nucleic acid fragments with a length of about 15 to about 35 nucleotides, are employed. These primers hybridize specifically onto the nucleic acid fragment to be detected. A plurality of amplification cycles then results in a particular DNA fragment being replicated and detected. If a fragment of this type can be detected, this means that the nucleic acid which is sought (in this case of KSHV) is present in the sample to be detected. The primers which can be employed according to the invention are thus short nucleic acid fragments with a length of 15 to 35 bases. These primers are preferably chosen at the 31 and 51 ends of the nucleic acid sequence specified above, a primer having in each case a sequence which is complementary to the stated nucleic acid sequence.

The polypeptides according to the invention can also be used for producing a vaccine against KSHV. For a vaccine of this type, the polypeptides according to the invention can also be combined with other proteins or polypeptides from KSHV. Immunization of the patients to be treated generates neutralizing antibodies which inactivate the virus when there is a threat of infection. An inoculation of this type is also conceivable if the patient to be treated is already infected by KSHV but the Kaposi sarcoma has not yet erupted.

Another aspect of the present invention relates to antibodies directed against the polypeptides according to the invention. These may comprise either polyclonal antibodies obtained by immunizing an animal (horse, bovine, goat) or monoclonal antibodies.

The technique for producing monoclonal antibodies was described by Kohler and Millstein in 1974 and currently represents a standard technology. This entails rodents (especially mice) being immunized and the thymus cells being fuzed to immortalized cells (cancer cell lines). These cell lines then produce monoclonal antibodies. However, for the purpose of the present invention, preferably humanized monoclonal antibodies are employed, because with these antibodies no unwanted immunological reactions are to be expected against the parts of the antibody not derived from humans. This entails transfer, by methods of genetic manipulation known per se, of the region coding for the variable region (Fab) of the antibodies from the mouse cell lines into cell lines which code for the required antibodies. This results in a human antibody which comprises in the variable regions sequences which are derived, for example, from mouse cell lines.

It has been found within the scope of the present invention, entirely surprisingly, that the polypeptides according to the invention have very considerable unexpected advantages for diagnosis and therapy. Worthy of special emphasis is the considerably stronger and more frequent reactivity of the polypeptides according to the invention with sera from Kaposi sarcoma patients, and the absence of cross-reactivity. For diagnosis it is particularly important that there is no cross-reactivity with other similar viruses such as, in particular, EBV. If there is cross-reactivity, this leads to false-positive results, because then antibodies directed against another virus (EBV) are incorrectly assessed as antibodies against KSHV.

EXPLANATION OF THE FIGURES

FIG. 1 shows the amino acid sequence of the polypeptide K8.1 according to the invention; the first 26 amino acids between the amino acids Met and Ala represent the signal peptide. The polypeptide according to the invention comprises the sequence up to the stop codon, that is to say up to and including Lys.

FIG. 2 depicts the nucleotide sequence coding for the polypeptide K8.1 according to the invention, including the signal peptide.

Figure 3:
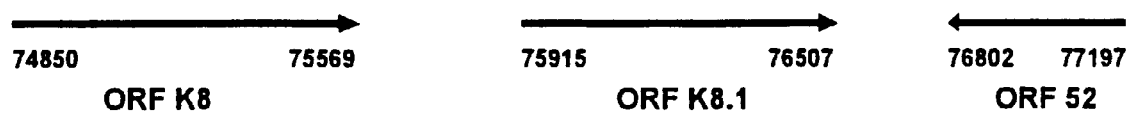
FIG. 3 shows the location of the open reading frame for the polypeptid K8.1 (ORF K8.1). The ORF K8.1 is located between the ORF K8 and the ORF52. In addition, the nucleotide positions of the three reading frames are indicated.

M: Rainbow marker; lane 1: HSB-2 cells (HHV-8 negative, control); lane 2: noninduced BCBL-1 cells; lane 3: BCBL-1 cells induced with TPA for 4 days, 20 ng/ml; lane 4: BCBL-1 cells induced with TPA for 4 days after digestion with PNGase F; lane 5: "mock" digestion, that is to say identical treatment of BCBL-1 cells as for the sample loaded in lane 4 but without addition of PNGase F.

Figure 5:
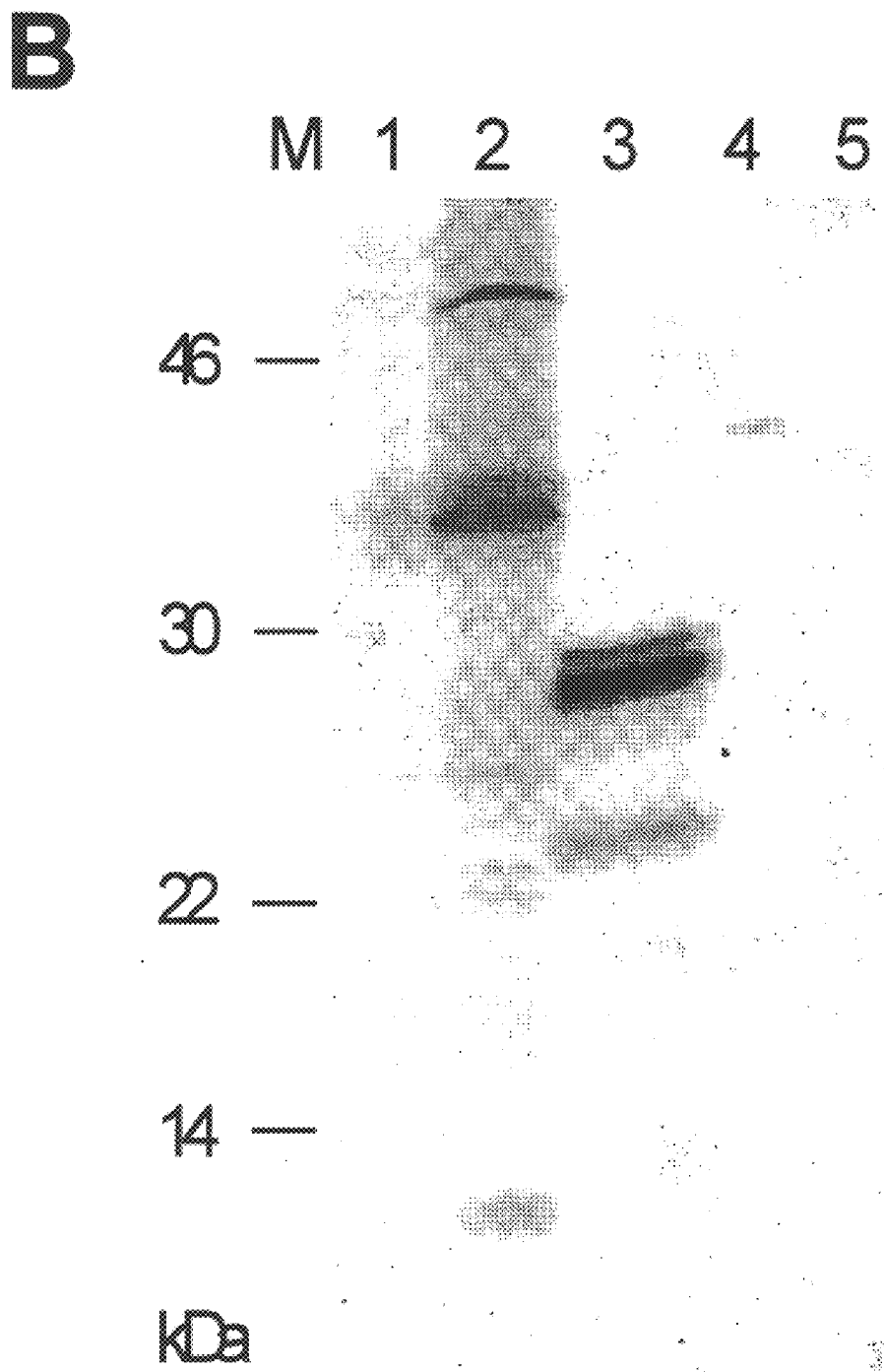

FIG. 5 shows that recombinant K8.1 polypeptide is recognized by a serum from a Kaposi sarcoma patient which also reacts with gp35/37. The migration behavior of the protein expressed in *E.coli* is identical to that observed with gp35/37 from BCBL-1 cells after endoglycosidase treatment.

The fractionation took place using a 15% polyacrylamide gel. The loadings on the individual lanes were:

M: Size standard; lane 1: BJAB cells; lane 2: BCBL-1 cells induced with TPA for 4 days; lane 3: recombinant polypeptide K8.1, 200 ng; lane 4: recombinant fusion protein with GST portion, the antigenic portion deriving from ORF65, 200 ng; lane 5: recombinant vIL-6, 200 ng.

Figure 4:
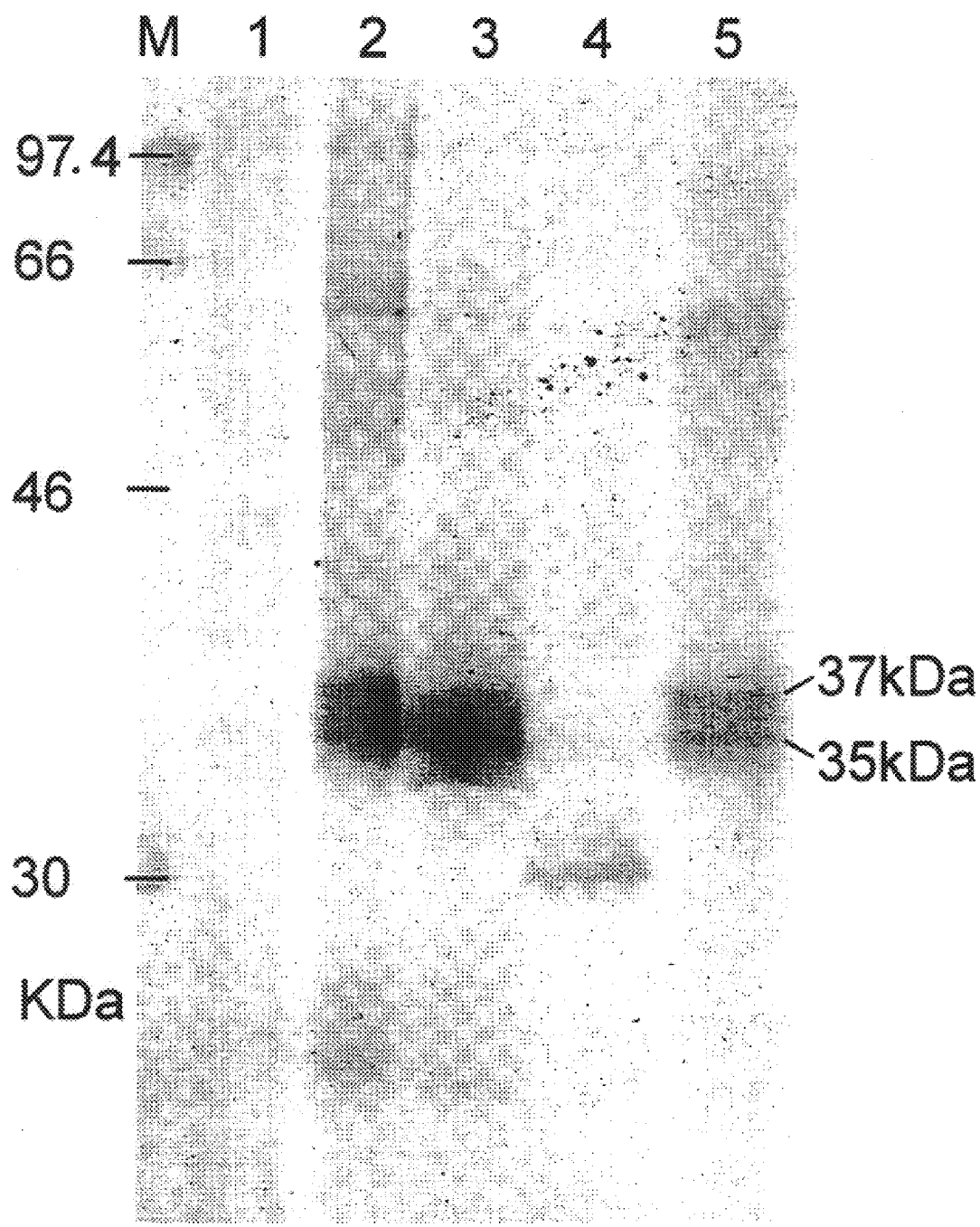
FIG. 4 shows the demonstration of the glycosylation of the immunogenic KSHV protein of 35 to 37 kDa (gp 35/37). A 12% polyacrylamide gel was used for the fractionation. A serum from an HIV-positive, KS-positive patient was used in a dilution of 1/200 in the Western blot. 45 µg of complete cellular protein in SDS sample buffer were loaded for each lane. The loadings on the individual lanes were.

The serum used in FIG. 5 was different from that in FIG. 4, and—differing from that used in FIG. 4—a third band can be seen in the region from 35 to 37 kDa. This clear, sharp band is readily identifiable in about 50% of all sera. This is very probably another viral protein since it differs from gp35/37 in being a sharp band not typical of glycoproteins. In addition, there is a serum from another HIV-positive, Kaposi sarcoma patient which shows only this relatively sharp band of 36 kDa, and not the two bands of gp35/37, in the Western blot with induced BCBL-1 cells. This serum does not recognize the recombinant polypeptide K8.1.

Figure 6:
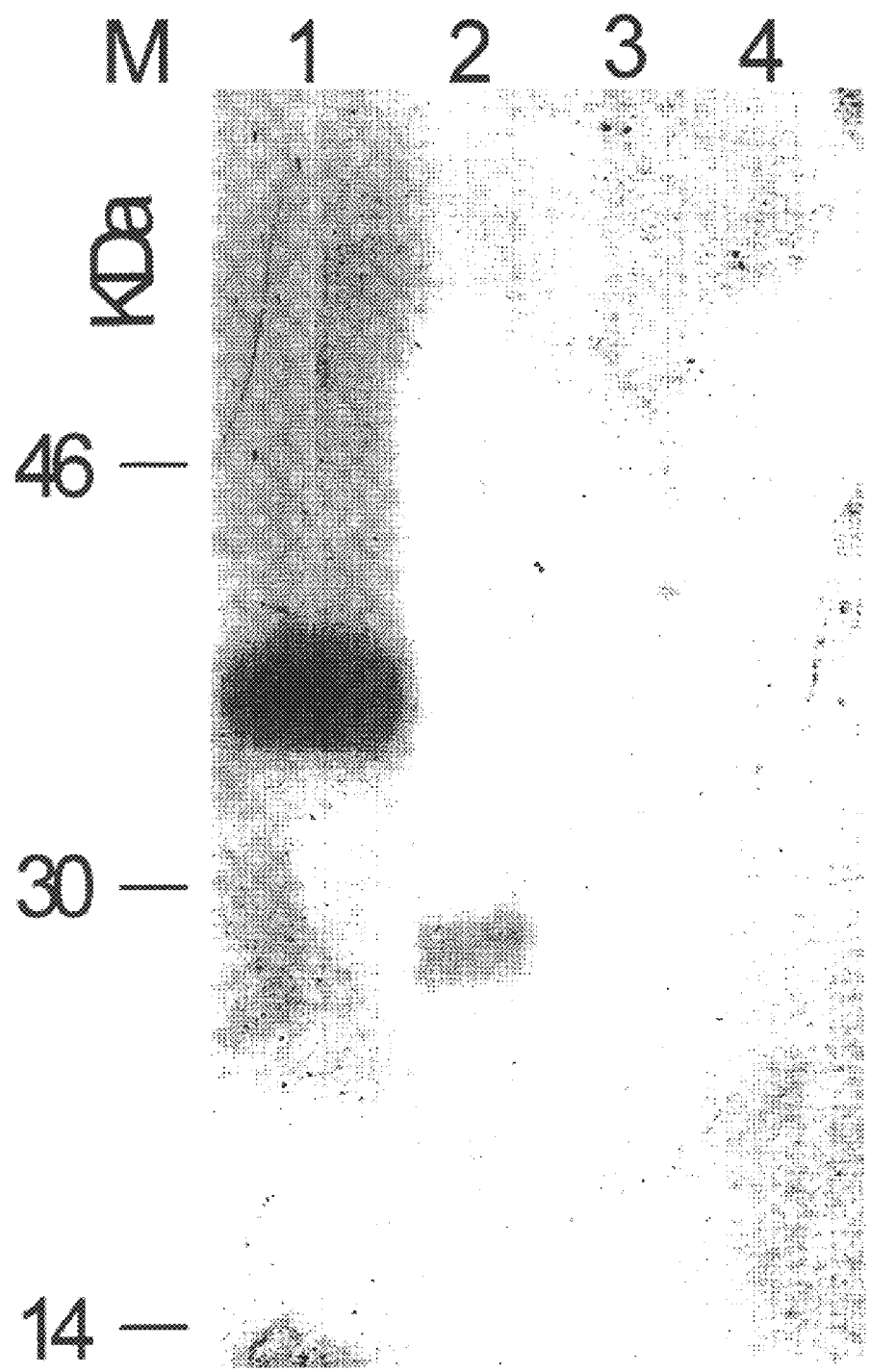

FIG. 6 shows the identity of the polypeptide K8.1 according to the invention with the glycoprotein gp35/37. The fractionation took place using a 15% polyacrylamide gel. Specific antibodies against recombinant polypeptide K8.1 were purified from the serum of an HIV-positive Kaposi sarcoma patient by binding to the recombinant polypeptide. These were employed in a dilution of 1/200. BCBL-1 cells induced with TPA for 4 days were loaded on lane 1. Recombinant polypeptide K8.1 (200 ng) was loaded on lane 2. Recombinant p18-GST was loaded in an amount of 200 ng on lane 3. p18-GST is a fusion protein with a GST portion and an ORF65 portion. Recombinant vIL-6, 200 ng, was loaded on lane 4.

The invention is explained in detail by the following examples.

EXAMPLE 1
Culturing of the cells

The KSHV (HHV-8)-positive BCBL-1 cells were obtained through the "AIDS Research and Reference Reagent" program. The HSB-1 and BJAB cells can be obtained straightforwardly from the ATCC. The cells were incubated in RPMI 1640 medium with 15% fetal calf serum, glutamine and gentamicin under standard conditions. For the TPA induction, the cells were induced with 20 ng/TPA at about $1 \times 10^6$ cells/ml. For the Western blots, the cells were washed twice in PBS standard buffer and resuspended in 1/100 of the initial volume of PBS, and the protein concentration was determined by the Pierce assay in accordance with the manufacturer's instructions.

EXAMPLE 2
Endoglycosidase F digestion

BCBL-1 cells were induced with TPA for 4 days. After washing twice in PBS, the cells were resuspended in 1% of the initial volume of PBS. 45 μl of this cell suspension, equivalent to 400 μg of total protein, were initially denatured in a 100 μl mixture with denaturation buffer (0.5% SDS, 1% β-mercaptoethanol) at 96° C. for 10 minutes. After addition of 15 μl of 10% NP-40 (Biolabs) and 15 μl of G7 cleavage buffer (Biolabs), digestion was carried out with 10,000 units of PNGase F (New England Biolabs) at 37° C. for 1 hour. 17 μl of this reaction mixture, equivalent to 45 μg of cellular protein, were used for the Western blot in FIG. 4, lane 4.

EXAMPLE 3
Protein gels and Western blot 12 and 15% protein gels with an acrylamide/bisacrylamide mixing ratio of 29/1 were prepared by standard protocols (Ausubel et al., *Current Protocols in Molecular Biology*, Wiley & Sons). After electrophoretic fractionation, the proteins were transferred from the polyacrylamide gel to nitrocellulose membranes (Schleicher & Schull) by electrophoresis using a semi-dry blot chamber from Hoefer in accordance with the manufacturer's instructions. Before incubation with the human serum, the nitrocellulose membranes were first preincubated in "blocking buffer" (150 mM NaCl, 20 mM tris pH 7.5, 0.5% Tween-20, 5% skim milk powder) at 4° C. overnight. Incubation with human sera took place at room temperature for 2 hours, likewise in blocking buffer, and the sera were always diluted 1/200. After washing 3 times in TBS-Tween (150 mM NaCl, 20 mM tris pH 7.5, 0.5% Tween) for 15 minutes each time, the sera were incubated with the 2nd antibody for 60 minutes (anti-human alkaline phosphatase conjugated antibodies from rabbits, Dako). The membranes were then washed firstly with 3x TBS-Tween and then washed 1x in TBS (150 mM NaCl, 20 mM tris pH 7.5) and stained with a substrate solution (RAD-free BCIP/NBT tablets, Schleicher & Schull) in accordance with the manufacturer's instructions.

EXAMPLE 4
Cloning and prokaryotic expression of KSHV polypeptide K8.1

The synthetic oligonucleotides K8-ImBam (gtgcggatccaattgtcccacgtatcgttc) and K8-1rHind (ggcaaagcttggcacacggttactagcacc) were used to amplify a fragment of the open reading frame K8.1 which comprises the coding region from amino acid 27 onwards. This corresponds to the presumed complete protein after elimination of the signal peptide. For the PCR, 100 ng of DNA from BCBL-1 cells were amplified in a 100 μl mixture with 100 ng of the above primers in each case in 30 cycles (95° C. 20 sec, 50° C. 20 sec, 72° C. 80 sec). The resulting DNA fragment was digested with HindIII and BamHI. 50 ng of the cleaved amplification product were ligated to 100 ng of the vector pQE9 (Quiagen), which had likewise been cleaved with BamHI and HindIII, in accordance with the manufacturer's instructions (T4 DNA Ligase, Gibco BRL). After transfection of the ligation mixture into the *E.coli* strain JM 109 (Stratagene Inc., La Jolla), a positive clone (pQK8-Im) was selected, and the nucleic acid sequence of the viral portion and of the vector sections important for prokaryotic expression (promoter, histidine taq) was determined. The nucleic acid sequence was checked using the ABI377 automatic sequencer (ABI Inc., Foster City, USA) in accordance with the manufacturer's protocols. To prepare and purify the recombinant protein K8.1 in *E.coli* JM 109, the bacteria were induced with 2 mM IPTG, lysed and purified by metal affinity chromatography under denaturing conditions as described by the manufacturer (Quiagen AG, Hilden: "The Quiaexpressionist", summer 1992 edition, pages 45 et seq.). The bacterial culture was induced at an OD600=0.6 with 2 mM IPTG and, after incubation at 37° C. for 3 h, centrifuged and lysed in 6 M guanidinium thiocyanate, 0.1 M sodium phosphate, 10 mM tris pH 8.0. The clarified supernatant was absorbed onto an Ni-NTA matrix and eluted with increasing concentrations of imidazole in 8 M urea, pH 6.5. The fractions were investigated for the protein content in a polyacrylamide gel (15%) after Comassie staining. The recombinant K8.1 eluted predominantly between 200 and 400 mM imidazole. For further use in Western blot and ELISA, the protein-containing fractions were pooled and dialyzed against 10 mM tris, pH 7.5, overnight. The calculated molecular weight of the protein expressed in this way is 20.4 kDa. The apparent molecular weight in the polyacrylamide gel is about 28 kDa.

EXAMPLE 5

Absorption of polypeptide K8.1-specific antibodies from human serum

400 μg of K8.1 polypeptide which had been expressed prokaryotically (plasmid pQK8-1m) and purified by affinity chromatography were fractionated in a 15% polyacrylamide gel and transferred to nitrocellulose membrane as described. The height of migration of the prokaryotically expressed protein was determined by staining with Ponceau red, and the corresponding region of the filter was cut out. After removal of the Ponceau red stain by washing several times in 150 mM NaCl, 20 mM tris, 1% Tween, the NC strip was initially incubated in blocking buffer at 20° C. for 4 h. Subsequently, the NC strip with the immobilized K8.1 protein was incubated with the $\frac{1}{200}$-diluted serum from a Kaposi sarcoma patient at 4° C. for 16 hours. After washing 4 times with TBS-Tween, the bound antibodies were eluted with 100 mM glycine, pH 2.9. This entailed the NC strip being incubated with the glycine solution for only 1 minute, and the solution being immediately neutralized with $\frac{1}{10}$ of the volume of 1 M tris, pH 9. The monospecific antibodies purified in this way were employed to demonstrate the identity of K8.1 with gp35/37 in the Western blot shown in Figure C (dilution $\frac{1}{200}$ based on the volume of the absorbed serum).

EXAMPLE 6

Results of the Western blot tests

The immunological reactivity of the various antigens with sera from different donors was investigated in the experiments. The results of the Western blots are summarized in Table 1.

TABLE 1

| | | Western blot reactivity | | |
|---|---|---|---|---|
| Serum | Category/Status | gp35/37nat | gp35/37rec | GST-ORF65 |
| 1 | HIV+, KS+ | + | + | + |
| 2 | HIV+, KS+ | + | + | + |
| 3 | HIV+, KS+ | + | + | + |
| 4 | HIV+, KS+ | + | + | + |
| 5 | HIV+, KS+ | + | + | + |
| 6 | HIV+, KS+ | + | + | + |
| 7 | HIV+, KS+ | + | + | ? |
| 8 | HIV+, KS+ | + | + | ? |
| 9 | HIV+, KS+ | + | + | − |
| 10 | HIV+, KS+ | + | + | − |
| 11 | HIV+, KS+ | + | + | − |
| 12 | HIV+, KS+ | + | + | − |
| 13 | HIV+, KS+ | + | + | − |
| 14 | HIV+, KS+ | + | + | − |
| 15 | HIV+, KS+ | + | + | − |
| 16 | HIV+, KS+ | + | + | − |
| 17 | HIV+, KS+ | + | + | − |
| 18 | HIV+, KS+ | + | + | − |
| 19 | HIV+, KS+ | + | + | − |
| 20 | HIV+, KS+ | + | + | − |
| 21 | HIV+, KS+ | + | + | − |
| 22 | HIV+, KS+ | ? | + | ? |
| 23 | HIV+, KS+ | − | − | ? |
| 24 | HIV+, KS+ | − | − | − |
| 25 | HIV+, KS+ | − | − | − |
| 26 | HIV+, KS+ | − | − | − |
| 27 | HIV+, KS+ | − | − | − |
| 28 | HIV−, KS+ | + | + | − |
| 29 | HIV−, KS+ | + | + | − |
| 30 | HIV+, KS− | − | − | − |
| 31 | HIV+, KS− | − | − | − |
| 32 | HIV+, KS− | − | − | − |
| 33 | HIV+, KS− | − | − | − |
| 34 | HIV+, KS− | − | − | − |
| 35 | HIV+, KS− | − | − | − |
| 36 | HIV+, KS− | − | − | − |
| 37 | HIV+, KS− | + | ? | + |
| 38 | HIV−, KS− | − | − | − |
| 39 | HIV−, KS− | − | − | − |
| 40 | HIV−, KS− | − | − | ? |
| 41 | EBV primary inf. | − | − | + |

Table 1 shows the Western blot results with the HHV-8 antigens and 41 human sera of various categories. Reactions: +=reactive band, i.e. positive reaction, ?=doubtful reaction, −=no band, i.e. negative reaction. The antigens employed were: gp35/37 nat=natural gp35/37 in extracts from induced BCBL-1 cells, unpurified; gp35/37 rec= recombinant histidine tag protein, without leader sequence, purified; GST-ORF65=recombinant GST (glutathione S-transferase) fusion protein with polypeptide from ORF65 of KSHV, purified. The results allow the following conclusions to be drawn:

The natural and the recombinant gp35/37 protein showed complete agreement with the various sera if two doubtful reactions (Nos. 22 and 37) are ignored for the present. This is a further indication of the identity. gp35/37 reacted positively with 24 of 29 sera from Kaposi patients, whereas ORF65 picked up only 10/29 as a maximum. This unambiguously proved the superiority of the polypeptides according to the invention. Only one of 12 KS-negative sera (No. 37) reacted with gp35/37. This serum from an HIV-positive person also reacted with GST-ORF65. Since HHV-8 antibodies are detectable even before clinical manifestation, such results are to be expected.

ORF65 additionally reacted with the serum from a patient with infectious mononuclease=EBV primary infection (No. 41). Although it cannot be precluded that a positive reaction was elicited by the fusion partner, gp35/37 was unambiguously the better antigen in these experiments.

EXAMPLE 7

Reactivity of the purified recombinant gp35/37 in an ELISA 100 ng of each of the purified recombinant antigens gp35/37, EBV GST p18 and GST ORF65, dissolved in 100 M of 0.01 M carbonate buffer pH 9.5, were in each case placed in a well of microtiter plates (Nunc, Maxisorp) and incubated in a grounded humidity chamber for 16 h. After addition of 100 μl of a calf serum-containing after-coating solution, the incubation was continued for 2 further hours. The plates were then emptied, carefully tapping out. The coated plates were subsequently used for the actual testing, or were stored, after drying in a vacuum cabinet with subsequent sealing in a tube of film, at −20° C. until used later. To carry out the test, the test wells of the ELISA plates were charged with 100 μl of a 1:21-diluted serum solution, sealed with a plastic film and incubated in an incubator (Binder, BED53) at 37° C. for 1 h. Washing three times in a Biotest Washer II was followed by conjugate incubation with 100 μl of mouse monoclonal antibodies directed against human IgG and labeled with peroxidase (30 min at 37°). After washing again, the bound antibodies were visualized through the peroxidase enzyme activity using 100 μl of 3,3',5,5'-tetramethylbenzidine (TMB, Sigma). The chromogenic reaction took 30 min at room temperature and was stopped by adding 100 μl of 1 N sulfuric acid. The optical density (OD) of the individual samples was measured at 495 nm (reference: 620 nm) in an Anthos HTII ELISA reader. All the OD values greater than 400 mOD were assessed as positive in the case of the HHV8-specific tests (gp35/37 and ORF65). A cut off of 0.15 OD was defined for the EBV-dependent test.

Results

ELISA tests were carried out to confirm the antigenic properties of the recombinant gp35/37 found in the Western blot experiments. For this purpose, sera from HIV patients with Kaposi sarcoma (KS+/HIV+) were tested, comparing with KS−/HIV+ and with sera from healthy blood donors (BD). All the values showing a ratio of OD to cut off (S/C ratio) greater than 1 were assessed as positive. A total of 9 of 10 sera (90%) from the KS+/HIV+ samples were positive with gp35/37, while 8/10 (80%) were positive with the recombinant ORF 65 antigen. This means that the sensitivity advantage of gp35/37 compared with ORF 65 is 10%. One sample (serum LD) from the KS−/HIV+ samples reacted with each of the two antigens. This may be a blood sample from an HIV patient who developed Kaposi carcinoma at a later date. It was not possible at the time of the invention to test a follow-up sample. In order to compare the two antigens for specificity, blood samples from healthy individuals were investigated. It was to be expected that no antibodies against HHV8 would be detectable in this group. As expected, all of 12 tested serum samples from blood donors (BD) were negative with gp35/37. One serum (Suhl 792) was assessed as positive with the ORF65 test, a fact which indicates a lower specificity of the antigen ORF65. In general, the results showed that, under the conditions used, the separation between positive and negative OD values was greater with gp35/37 than with ORF65. The S/C ratios are distinctly higher with gp35/37, expressing the fact that the immunogenic reactivity of the antigen is better than that of ORF65.

Numerous reading frames of HHV8 show sequence homologies with the EBV genome. It was intended in this regard to examine whether sera with a high titer of antibodies against EBV cross-react with gp35/37. For this purpose, 7 sera from nasopharyngeal carcinoma (NPC) patients, who are known to show high titers against EBV antigens, were tested. The positive control used was the recombinant EBV virus capsid protein (VCA) p18 as GST fusion protein. All NPC sera were negative with gp35/37. Three sera, C6, C19 and C28, were positive with ORF65, and all sera were highly positive with EBV p18 VCA antigen. The results showed that the possibility of cross-reactivity with gp35/37 can be ruled out. By contrast, a cross-reactivity was observable with the HHV 8 antigen ORF65.

In summary, it is evident that the recombinant antigen gp35/37 provides both better reactivity and a higher specificity than ORF65. In order to underline the reactivity advantages of the recombinant gp35/37, 50 commercially obtainable sera (BioClinical Partners) from HIV-positive homosexual men (KS risk) from San Francisco were tested. According to statements in the literature, this group of patients has an increased risk of developing Kaposi sarcoma. Of the 50 sera tested, 29 (58%) were positive with gp35/37, and a total of 7 (14%) were positive with ORF65. The results show that the antigen gp35/37 provides high sensitivity as diagnostic marker and can be employed as reliable seromarker.

The results of this experiment have been summarized in Tables 2 and 3.

TABLE 2

|  | gp35/37 | EBV GST p18 | HHV 8 GST ORF65 |
|---|---|---|---|
| KS+/HIV+ | | | |
| 26295 | 6.9 | 20.0 | 1.3 |
| 22675 | 7.0 | 20.0 | 1.2 |
| 26673 | 7.5 | 20.0 | 1.2 |
| 43742 | 7.5 | 20.0 | 2.0 |
| 23971 | 6.9 | 20.0 | 0.5 |
| 43630 | 4.5 | 20.0 | 3.0 |
| 5942 | 0.5 | 20.0 | 0.5 |
| SH | 3.0 | 20.0 | 1.1 |
| BP | 1.1 | 20.0 | 1.2 |
| AC(53) | 6.5 | 20.0 | 1.8 |
| KS−/HIV+ | | | |
| MM | 0.4 | 20.0 | 0.3 |
| WU | 0.6 | 20.0 | 0.8 |
| FP | 0.6 | 13.1 | 0.6 |
| L D | 1.0 | 20.0 | 3.4 |
| RK | 0.7 | 0.9 | 0.6 |
| D J | 0.5 | 1.0 | 0.6 |
| A E | 0.6 | 20.0 | 0.4 |
| AP | 0.5 | 4.2 | 0.5 |
| BD | | | |
| Suhl 789 | 0.2 | 20.0 | 0.6 |
| Suhl 790 | 0.3 | 12.9 | 0.4 |
| Suhl 791 | 0.3 | 20.0 | 0.7 |
| Suhl 792 | 0.2 | 20.0 | 1.0 |
| Suhl 793 | 0.1 | 18.4 | 0.3 |
| Suhl 794 | 0.2 | 20.0 | 0.4 |
| Suhl 795 | 0.2 | 20.0 | 0.3 |
| Suhl 796 | 0.2 | 20.0 | 0.4 |
| Suhl 797 | 0.1 | 13.9 | 0.4 |
| Suhl 798 | 0.2 | 18.0 | 0.4 |
| Suhl 799 | 0.2 | 20.0 | 0.4 |
| Suhl 800 | 0.2 | 20.0 | 0.4 |
| NPC | | | |
| C 6 | 0.4 | 17.6 | 1.7 |
| C 9 | 0.2 | 18.6 | 0.8 |
| C 10 | 0.3 | 20.0 | 0.8 |
| C 19 | 0.3 | 20.0 | 1.1 |
| C 21 | 0.2 | 20.0 | 0.6 |
| C 22 | 0.4 | 20.0 | 0.7 |
| C 28 | 0.2 | 20.0 | 1.1 |

TABLE 3

| KS risk | gp35/37 | EBV GST p18 | HHV8 GST ORF 65 |
|---|---|---|---|
| 0744 | 0.8 | 18.7 | 0.5 |
| 0745 | 7.5 | 17.3 | 1.2 |
| 0746 | 0.7 | 20.0 | 0.3 |
| 0747 | 0.5 | 17.3 | 0.2 |
| 0748 | 0.6 | 20.0 | 0.5 |
| 0749 | 7.5 | 18.3 | 0.4 |
| 0750 | 2.7 | 15.2 | 1.8 |
| 0751 | 0.7 | 18.5 | 0.3 |
| 0752 | 0.7 | 20.0 | 0.3 |
| 0753 | 2.1 | 20.0 | 0.4 |
| 0754 | 2.0 | 20.0 | 0.7 |

TABLE 3-continued

| KS risk | EBV gp35/37 | GST p18 | HHV8 GST ORF 65 |
|---|---|---|---|
| 0755 | 0.6 | 16.4 | 0.3 |
| 0756 | 0.5 | 20.0 | 0.3 |
| 0757 | 2.6 | 20.0 | 0.3 |
| 0758 | 0.7 | 18.4 | 0.3 |
| 0759 | 0.5 | 18.5 | 0.4 |
| 0760 | 1.3 | 20.0 | 0.4 |
| O761 | 7.5 | 20.0 | 0.9 |
| 0762 | 7.5 | 20.0 | 1.2 |
| 0763 | 0.8 | 20.0 | 1.1 |
| 0764 | 2.5 | 20.0 | 0.3 |
| 0765 | 0.9 | 20.0 | 0.3 |
| 0766 | 7.5 | 20.0 | 0.7 |
| 0767 | 1.7 | 20.0 | 0.2 |
| 0768 | 0.9 | 20.0 | 0.5 |
| 0769 | 0.5 | 20.0 | 0.2 |
| 0770 | 0.3 | 20.0 | 0.2 |
| 0771 | 3.2 | 20.0 | 0.3 |
| 0772 | 2.0 | 20.0 | 0.3 |
| 0773 | 6.1 | 20.0 | 0.6 |
| 0774 | 4.0 | 19.0 | 0.3 |
| 0775 | 7.5 | 18.4 | 0.3 |
| 0776 | 0.8 | 18.7 | 0.4 |
| 0777 | 7.5 | 18.5 | 0.6 |
| 0778 | 0.5 | 17.9 | 0.3 |
| 0779 | 7.5 | 18.4 | 1.7 |
| 0780 | 7.5 | 18.6 | 0.7 |
| 0781 | 1.1 | 17.6 | 0.5 |
| 0782 | 2.6 | 20.0 | 0.4 |
| 0783 | 7.5 | 18.4 | 1.5 |
| 0784 | 1.0 | 20.0 | 0.3 |
| 0785 | 7.5 | 20.0 | 0.8 |
| 0786 | 7.5 | 20.0 | 0.7 |
| 0787 | 6.1 | 20.0 | 0.3 |
| 0788 | 0.8 | 20.0 | 0.2 |
| 0789 | 2.1 | 16.7 | 0.3 |
| 0790 | 0.3 | 19.0 | 0.5 |
| 0791 | 0.6 | 20.0 | 0.5 |
| 0792 | 0.9 | 18.6 | 0.7 |
| 0793 | 6.4 | 17.8 | 1.0 |
| % | 58% | 100% | 14% |

What is claimed is:

1. An immunogenic polypeptide, comprising at least 10 consecutive amino acids from the sequence of amino acids set forth in SEQ ID No. 2.

2. A polypeptide of claim 1, comprising at least 10 consecutive amino acids from the sequence of amino acids set forth as amino acids numbered 27–197 of SEQ ID No.2.

3. A polypeptide of claim 1 that comprises at least 14 consecutive amino acids from the sequence of amino acids.

4. A polypeptide of claim 1 that comprises at least 25 consecutive amino acids from the sequence of amino acids.

5. A polypeptide of claim 1 that comprises at least 30 consecutive amino acids from the sequence of amino acids.

6. A polypeptide of claim 1 that comprises at least 40 consecutive amino acids from the sequence of amino acids.

7. A polypeptide of claim 1 that is encoded by the Kaposi sarcoma-associated herpes virus.

8. A polypeptide of claim 1 that reacts with antibodies that are specific for the Kaposi sarcoma-associated herpes virus.

9. A composition, comprising a polypeptide of claim 1 in a pharmaceutically acceptable vehicle.

10. A polypeptide of claim 1, that is immunogenic.

11. A composition, comprising a polypeptide of claim 1 in a vehicle formulated for performing an immunodiagnostic assay.

12. A test kit for detecting antibodies indicative of infection with a Kaposi sarcoma-associated herpes virus in a human or mammal, comprising a polypeptide of claim 1.

13. The test kit of claim 12, further comprising a reagent for detecting a complex comprising a polypeptide of claim 1 and at least one antibody specifically bound thereto.

14. The test kit of claim 13, wherein the reagent is an anti-antibody.

15. The test kit of claim 13, further comprising an additional antibody that is specific for a polypeptide that comprises at least 10 consecutive amino acids from SEQ ID No. 1.

16. The test kit of claim 13, wherein the reagent for detecting the complex is labeled.

17. The test kit of claim 16, wherein the label is an enzyme.

18. The test kit of claim 12, wherein the polypeptide is labeled.

19. A method for detecting antibodies indicative of infection of a mammal with a Kaposi sarcoma-associated herpes virus, comprising:
    reacting a polypeptide of claim 1 with serum or a component thereof from the mammal, wherein reaction of the polypeptide with the serum is indicative of infection.

20. The method of claim 19 that is an immunodiagnostic assay.

21. An immunogenic composition, comprising a polypeptide of claim 1.

22. The method of claim 19 that is an immunoblot assay.

23. The method of claim 19 that is an western blot assay.

24. The method of claim 19 that is a enzyme linked immunoabsorbent assay (ELISA).

25. A polypeptide of claim 1 that is produced in a prokaryotic host.

26. A polypeptide of claim 1 that is produced in a eukaryotic host.

27. A polypeptide of claim 1 that produced by chemical synthesis.

28. A polypeptide of claim 2 that comprises at least 14 consecutive amino acids from the sequence of amino acids.

29. A polypeptide of claim 2 that comprises at least 25 consecutive amino acids from the sequence of amino acids.

30. A polypeptide of claim 2 that comprises at least 30 consecutive amino acids from the sequence of amino acids.

31. A polypeptide of claim 2 that comprises at least 40 consecutive amino acids from the sequence of amino acids.

32. A polypeptide of claim 2 that is encoded by the Kaposi sarcoma-associated herpes virus.

33. A polypeptide of claim 2 that reacts with antibodies that are specific for the Kaposi sarcoma-associated herpes virus.

34. An immunogenic composition, comprising a polypeptide of claim 2.

\* \* \* \* \*

SEQUENCE LISTING

<160> NUMBER OF SEQ ID NOS: 2

<210> SEQ ID NO 1
<211> LENGTH: 594
<212> TYPE: DNA
<213> ORGANISM: Kaposi's sarcoma-associated herpesvirus

<400> SEQUENCE: 1

```
atgagttcca cacagattcg cacagaaatc cctgtggcgc tcctaatcct atgcctttgt    60
ctggtggcgt gccatgccaa ttgtcccacg tatcgttcgc attgggatt ctggcaagag    120
ggttggagtg gacaggttta tcaggactgg ctaggcagga tgaactgttc ctacgagaat   180
atgacggccc tagaggccgt ctccctaaac gggaccagac tagcagctgg atctccgtcg   240
agtgagtatc caaatgtctc cgtatctgtt gaagatacgt ctgcctctgg gtctggagaa   300
gatgcaatag atgaatcggg gtcgggggag gaagagcgtc ccgtgacctc ccacgtgact   360
tttatgacac aaagcgtcca ggccaccaca gaactgaccg atgccttaat atcagccttt   420
tcaggtgtat tacacgtttc aactgtaatc cctcgcaatt gggtaaaccg tcggtgtgta   480
gggataaagc gtaaccttac gttctgtctc atctacagga tcatattcat ctggggaacc   540
atccaggacc acgcgaattc gcgtatcacc ggtcgcagaa aacggcagaa atag          594
```

<210> SEQ ID NO 2
<211> LENGTH: 197
<212> TYPE: PRT
<213> ORGANISM: Kaposi's sarcoma-associated herpesvirus

```
<400> SEQUENCE: 2

Met Ser Ser Thr Gln Ile Arg Thr Glu Ile Pro Val Ala Leu Leu Ile
 1               5                  10                  15

Leu Cys Leu Cys Leu Val Ala Cys His Ala Asn Cys Pro Thr Tyr Arg
                20                  25                  30

Ser His Leu Gly Phe Trp Gln Glu Gly Trp Ser Gly Gln Val Tyr Gln
            35                  40                  45

Asp Trp Leu Gly Arg Met Asn Cys Ser Tyr Glu Asn Met Thr Ala Leu
        50                  55                  60

Glu Ala Val Ser Leu Asn Gly Thr Arg Leu Ala Ala Gly Ser Pro Ser
65                  70                  75                  80

Ser Glu Tyr Pro Asn Val Ser Val Ser Val Glu Asp Thr Ser Ala Ser
                85                  90                  95

Gly Ser Gly Glu Asp Ala Ile Asp Glu Ser Gly Ser Gly Glu Glu Glu
                100                 105                 110

Arg Pro Val Thr Ser His Val Thr Phe Met Thr Gln Ser Val Gln Ala
            115                 120                 125

Thr Thr Glu Leu Thr Asp Ala Leu Ile Ser Ala Phe Ser Gly Val Leu
    130                 135                 140

His Val Ser Thr Val Ile Pro Arg Asn Trp Val Asn Arg Arg Cys Val
145                 150                 155                 160

Gly Ile Lys Arg Asn Leu Thr Phe Cys Leu Ile Tyr Arg Ile Ile Phe
                165                 170                 175

Ile Trp Gly Thr Ile Gln Asp His Ala Asn Ser Arg Ile Thr Gly Arg
            180                 185                 190

Arg Lys Arg Gln Lys
            195
```